(12) United States Patent
Diekhans et al.

(10) Patent No.: US 11,699,551 B2
(45) Date of Patent: Jul. 11, 2023

(54) DEVICE FOR INDUCTIVE ENERGY TRANSMISSION IN A HUMAN BODY AND USE OF THE DEVICE

(71) Applicant: KARDION GMBH, Stuttgart (DE)

(72) Inventors: Tobias Diekhans, Stuttgart (DE); Samuel Vasconcelos Araujo, Esslingen (DE); Michael Jiptner, Besigheim (DE)

(*) Notice: Subject to any disclaimer, the term of this patent is extended or adjusted under 35 U.S.C. 154(b) by 53 days.

(21) Appl. No.: 17/090,355

(22) Filed: Nov. 5, 2020

(65) Prior Publication Data

US 2022/0139614 A1  May 5, 2022

(51) Int. Cl.
| | |
|---|---|
| A61M 60/876 | (2021.01) |
| H01F 38/14 | (2006.01) |
| H02J 50/12 | (2016.01) |
| A61M 60/873 | (2021.01) |
| H01F 27/24 | (2006.01) |

(52) U.S. Cl.
CPC ........... *H01F 38/14* (2013.01); *A61M 60/873* (2021.01); *A61M 60/876* (2021.01); *H01F 27/24* (2013.01); *H02J 50/12* (2016.02)

(58) Field of Classification Search
CPC .................................................. A61M 60/876
See application file for complete search history.

(56) References Cited

U.S. PATENT DOCUMENTS

| | | |
|---|---|---|
| 2,254,698 A | 9/1941 | Hansen, Jr. |
| 3,085,407 A | 4/1963 | Tomlinson |
| 3,614,181 A | 10/1971 | Meeks |
| 3,645,268 A | 2/1972 | Capote |
| 3,747,998 A | 7/1973 | Klein et al. |
| 3,807,813 A | 4/1974 | Milligan |
| 4,888,009 A | 12/1989 | Lederman et al. |
| 4,888,011 A | 12/1989 | Kung et al. |
| 4,896,754 A | 1/1990 | Carlson et al. |
| 5,000,177 A | 3/1991 | Hoffmann et al. |
| 5,195,877 A | 3/1993 | Kletschka |
| 5,289,821 A | 3/1994 | Swartz |
| 5,443,503 A | 8/1995 | Yamane |
| 5,599,173 A | 2/1997 | Chen et al. |
| 5,613,935 A | 3/1997 | Jarvik |
| 5,629,661 A * | 5/1997 | Ooi .......... H01F 27/36 336/215 |
| 5,690,674 A | 11/1997 | Diaz |
| 5,713,954 A | 2/1998 | Rosenberg et al. |
| 5,766,207 A | 6/1998 | Potter et al. |
| 5,843,141 A | 12/1998 | Bischoff et al. |
| 5,888,242 A | 3/1999 | Antaki et al. |

(Continued)

FOREIGN PATENT DOCUMENTS

| | | |
|---|---|---|
| CA | 3 000 581 | 4/2017 |
| CN | 103143072 | 6/2013 |

(Continued)

*Primary Examiner* — Daniel Kessie
(74) *Attorney, Agent, or Firm* — Knobbe, Martens, Olson & Bear, LLP

(57) ABSTRACT

The invention relates to a device (10) for inductive energy transmission into a human body (1), having a transmitter coil (24) and/or a receiver coil (14) having a first magnetic core (26) and a resonance or choke coil (16, 34) having a second magnetic core (32), wherein the first magnetic core (26) forms a part of the second magnetic core (32).

10 Claims, 1 Drawing Sheet

(56) References Cited

U.S. PATENT DOCUMENTS

| | | |
|---|---|---|
| 6,058,958 A | 5/2000 | Benkowski et al. |
| 6,212,430 B1 | 4/2001 | Kung et al. |
| 6,224,540 B1 | 5/2001 | Lederman et al. |
| 6,254,359 B1 | 7/2001 | Aber |
| 6,264,601 B1 | 7/2001 | Jassawalla et al. |
| 6,324,430 B1 | 11/2001 | Zarinetchi et al. |
| 6,324,431 B1 | 11/2001 | Zarinetchi et al. |
| 6,361,292 B1 | 3/2002 | Chang et al. |
| 6,366,817 B1 | 4/2002 | Kung |
| 6,389,318 B1 | 5/2002 | Zarinetchi et al. |
| 6,398,734 B1 | 6/2002 | Cimochowski et al. |
| 6,400,991 B1 | 6/2002 | Kung |
| 6,442,434 B1 | 8/2002 | Zarinetchi et al. |
| 6,445,956 B1 | 9/2002 | Laird et al. |
| 6,471,713 B1 | 10/2002 | Vargas et al. |
| 6,496,733 B2 | 12/2002 | Zarinetchi et al. |
| 6,508,756 B1 | 1/2003 | Kung et al. |
| 6,527,698 B1 | 3/2003 | Kung et al. |
| 6,530,876 B1 | 3/2003 | Spence |
| 6,540,658 B1 | 4/2003 | Fasciano et al. |
| 6,561,975 B1 | 5/2003 | Pool et al. |
| 6,592,620 B1 | 7/2003 | Lancisi et al. |
| 6,979,338 B1 | 12/2005 | Loshakove et al. |
| 7,062,331 B2 | 6/2006 | Zarinetchi et al. |
| 7,070,398 B2 | 7/2006 | Olsen et al. |
| 7,155,291 B2 | 12/2006 | Zarinetchi et al. |
| 7,160,243 B2 | 1/2007 | Medvedev |
| 7,338,521 B2 | 3/2008 | Antaki et al. |
| 7,513,864 B2 | 4/2009 | Kantrowitz et al. |
| 7,520,850 B2 | 4/2009 | Brockway |
| 7,762,941 B2 | 7/2010 | Jarvik |
| 7,794,384 B2 | 9/2010 | Sugiura et al. |
| 7,819,916 B2 | 10/2010 | Yaegashi |
| 7,942,805 B2 | 5/2011 | Shambaugh, Jr. |
| 7,959,551 B2 | 6/2011 | Jarvik |
| 8,012,079 B2 | 9/2011 | Delgado, III |
| 8,075,472 B2 | 12/2011 | Zilbershlag et al. |
| 8,088,059 B2 | 1/2012 | Jarvik |
| 8,231,519 B2 | 7/2012 | Reichenbach et al. |
| 8,489,200 B2 | 7/2013 | Zarinetchi et al. |
| 8,608,635 B2 | 12/2013 | Yomtov et al. |
| 8,612,002 B2 | 12/2013 | Faltys et al. |
| 8,620,447 B2 | 12/2013 | D'Ambrosio et al. |
| 8,766,788 B2 | 7/2014 | D'Ambrosio |
| 8,827,890 B2 | 9/2014 | Lee et al. |
| 8,862,232 B2 | 10/2014 | Zarinetchi et al. |
| 8,870,739 B2 | 10/2014 | LaRose et al. |
| 8,900,114 B2 | 12/2014 | Tansley et al. |
| 8,961,389 B2 | 2/2015 | Zilbershlag |
| 9,002,468 B2 | 4/2015 | Shea et al. |
| 9,002,469 B2 | 4/2015 | D'Ambrosio |
| 9,220,826 B2 | 12/2015 | D'Ambrosio |
| 9,283,314 B2 | 3/2016 | Prasad et al. |
| 9,381,286 B2 | 7/2016 | Spence et al. |
| 9,440,013 B2 | 9/2016 | Dowling et al. |
| 9,456,898 B2 | 10/2016 | Barnes et al. |
| 9,486,566 B2 | 11/2016 | Siess |
| 9,492,600 B2 | 11/2016 | Strueber et al. |
| 9,539,094 B2 | 1/2017 | Dale et al. |
| 9,561,362 B2 | 2/2017 | Malinowski |
| 9,569,985 B2 | 2/2017 | Alkhatib et al. |
| 9,592,397 B2 | 3/2017 | Hansen et al. |
| 9,603,984 B2 | 3/2017 | Romero et al. |
| 9,616,107 B2 | 4/2017 | VanAntwerp et al. |
| 9,713,701 B2 | 7/2017 | Sarkar et al. |
| 9,717,831 B2 | 8/2017 | Schuermann |
| 9,724,083 B2 | 8/2017 | Quadri et al. |
| 9,800,172 B1 | 10/2017 | Leabman |
| 9,833,314 B2 | 12/2017 | Corbett |
| 9,833,611 B2 | 12/2017 | Govea et al. |
| 9,848,899 B2 | 12/2017 | Sliwa et al. |
| 10,143,571 B2 | 12/2018 | Spence et al. |
| 10,463,508 B2 | 11/2019 | Spence et al. |
| 11,000,282 B2 | 5/2021 | Schuelke et al. |
| 11,056,878 B2 | 7/2021 | Gao et al. |
| 11,065,437 B2 | 7/2021 | Aber et al. |
| 11,103,715 B2 * | 8/2021 | Fort .............. H02J 50/50 |
| 11,110,265 B2 | 9/2021 | Johnson |
| 11,179,559 B2 | 11/2021 | Hansen |
| 11,224,737 B2 | 1/2022 | Petersen et al. |
| 11,291,826 B2 | 4/2022 | Tuval et al. |
| 11,317,988 B2 | 5/2022 | Hansen et al. |
| 11,344,717 B2 | 5/2022 | Kallenbach et al. |
| 11,351,359 B2 | 6/2022 | Clifton et al. |
| 11,351,360 B2 | 6/2022 | Rudser et al. |
| 11,368,081 B2 | 6/2022 | Vogt et al. |
| 2003/0040765 A1 | 2/2003 | Breznock |
| 2003/0125766 A1 | 7/2003 | Ding |
| 2003/0130581 A1 | 7/2003 | Salo et al. |
| 2004/0167410 A1 | 8/2004 | Hettrick |
| 2005/0006083 A1 | 1/2005 | Chen et al. |
| 2006/0004423 A1 | 1/2006 | Boveja et al. |
| 2006/0190036 A1 | 8/2006 | Wendel et al. |
| 2006/0196277 A1 | 9/2006 | Allen et al. |
| 2007/0129767 A1 | 6/2007 | Wahlstrand |
| 2007/0282209 A1 | 12/2007 | Lui et al. |
| 2008/0015481 A1 | 1/2008 | Bergin et al. |
| 2008/0079392 A1 | 4/2008 | Baarman |
| 2008/0082005 A1 | 4/2008 | Stern et al. |
| 2009/0024042 A1 | 1/2009 | Nunez et al. |
| 2009/0198307 A1 | 8/2009 | Mi et al. |
| 2009/0198312 A1 | 8/2009 | Barker |
| 2009/0276016 A1 | 11/2009 | Phillips et al. |
| 2009/0312650 A1 | 12/2009 | Maile et al. |
| 2011/0137394 A1 | 6/2011 | Lunsford et al. |
| 2011/0224720 A1 | 9/2011 | Kassab et al. |
| 2012/0022645 A1 | 1/2012 | Burke |
| 2012/0050931 A1 | 3/2012 | Terry et al. |
| 2012/0158074 A1 | 6/2012 | Hall |
| 2013/0099585 A1 | 4/2013 | Von Novak et al. |
| 2013/0116575 A1 | 5/2013 | Mickle et al. |
| 2013/0303970 A1 | 11/2013 | Keenan et al. |
| 2014/0012282 A1 | 1/2014 | Fritsch |
| 2014/0039587 A1 | 2/2014 | Romero |
| 2014/0063666 A1 | 3/2014 | Kallal et al. |
| 2014/0094645 A1 | 4/2014 | Lafontaine et al. |
| 2014/0104898 A1 | 4/2014 | Yeo et al. |
| 2014/0107754 A1 | 4/2014 | Fuhs et al. |
| 2014/0135884 A1 | 5/2014 | Tockman et al. |
| 2014/0233184 A1* | 8/2014 | Thompson .............. H02J 50/10 |
| | | 361/692 |
| 2014/0265620 A1 | 9/2014 | Hoarau et al. |
| 2015/0028805 A1 | 1/2015 | Dearden et al. |
| 2015/0090372 A1 | 4/2015 | Branagan et al. |
| 2015/0196076 A1 | 7/2015 | Billingslea |
| 2015/0290373 A1 | 10/2015 | Rudser et al. |
| 2015/0333532 A1* | 11/2015 | Han .............. H02J 50/005 |
| 2015/0380972 A1 | 12/2015 | Fort |
| 2016/0022889 A1 | 1/2016 | Bluvshtein et al. |
| 2016/0067395 A1 | 3/2016 | Jimenez et al. |
| 2016/0081680 A1 | 3/2016 | Taylor |
| 2016/0175501 A1 | 6/2016 | Schuermann |
| 2016/0271309 A1 | 9/2016 | Throckmorton et al. |
| 2016/0331980 A1 | 11/2016 | Strommer et al. |
| 2016/0344302 A1 | 11/2016 | Inoue |
| 2017/0047781 A1 | 2/2017 | Stanislawski et al. |
| 2017/0136164 A1 | 5/2017 | Yeatts |
| 2017/0143977 A1 | 5/2017 | Kaib et al. |
| 2017/0203104 A1 | 7/2017 | Nageri et al. |
| 2017/0271919 A1 | 9/2017 | Von Novak, III et al. |
| 2017/0288448 A1* | 10/2017 | Kranz .............. H04B 5/0037 |
| 2017/0354812 A1 | 12/2017 | Callaghan et al. |
| 2018/0078329 A1 | 3/2018 | Hansen et al. |
| 2018/0207336 A1 | 7/2018 | Solem |
| 2018/0256796 A1 | 9/2018 | Hansen |
| 2018/0256800 A1 | 9/2018 | Conyers et al. |
| 2019/0068004 A1 | 2/2019 | Louis |
| 2019/0097447 A1 | 3/2019 | Partovi |
| 2019/0175808 A1 | 6/2019 | Zilbershlag et al. |
| 2019/0222064 A1 | 7/2019 | Du et al. |
| 2019/0344000 A1 | 11/2019 | Kushwaha et al. |
| 2019/0351120 A1 | 11/2019 | Kushwaha et al. |
| 2019/0393735 A1 | 12/2019 | Lee et al. |
| 2020/0054806 A1 | 2/2020 | Sun |

(56) References Cited

U.S. PATENT DOCUMENTS

| | | | |
|---|---|---|---|
| 2020/0139032 A1 | 5/2020 | Bryson et al. | |
| 2020/0227954 A1* | 7/2020 | Ding | H02J 50/10 |
| 2020/0350812 A1 | 11/2020 | Vogt et al. | |
| 2021/0057804 A1 | 2/2021 | Wenning | |
| 2021/0143688 A1 | 5/2021 | Agrawal et al. | |
| 2021/0290931 A1 | 9/2021 | Baumbach | |
| 2021/0322011 A1 | 10/2021 | Schuelke et al. | |
| 2021/0336484 A1 | 10/2021 | Araujo et al. | |
| 2021/0339009 A1 | 11/2021 | Stotz et al. | |
| 2021/0351628 A1 | 11/2021 | Araujo et al. | |
| 2021/0379360 A1 | 12/2021 | Schellenberg | |
| 2021/0386990 A1 | 12/2021 | Stotz et al. | |
| 2021/0393944 A1 | 12/2021 | Wenning | |
| 2021/0399582 A1 | 12/2021 | Araujo et al. | |
| 2022/0080184 A1 | 3/2022 | Clifton et al. | |
| 2022/0080185 A1 | 3/2022 | Clifton et al. | |
| 2022/0320901 A1 | 10/2022 | Araujo et al. | |
| 2022/0407403 A1 | 12/2022 | Vogt et al. | |

FOREIGN PATENT DOCUMENTS

| | | |
|---|---|---|
| CN | 103942511 | 7/2014 |
| CN | 104274873 | 1/2015 |
| CN | 104888293 | 3/2017 |
| CN | 106776441 | 5/2017 |
| DE | 103 02 550 | 8/2004 |
| DE | 10 2012 200 912 | 7/2013 |
| DE | 11 2012 005 944 | 12/2014 |
| DE | 10 2016 106 683 | 10/2016 |
| DE | 10 2018 206 758 | 11/2019 |
| EP | 0 930 086 | 7/1999 |
| EP | 2 752 209 | 7/2014 |
| EP | 2 782 210 | 9/2014 |
| EP | 2 859 911 | 4/2015 |
| EP | 2 966 753 | 1/2016 |
| EP | 2 454 799 | 9/2016 |
| EP | 2 709 689 | 4/2017 |
| EP | 3 220 505 | 9/2017 |
| EP | 3 423 126 | 2/2021 |
| EP | 3 198 677 | 3/2021 |
| EP | 3 248 647 | 3/2021 |
| EP | 3 436 106 | 3/2021 |
| EP | 3 436 105 | 4/2021 |
| EP | 3 116 407 | 5/2021 |
| EP | 2 608 731 | 7/2021 |
| EP | 3 077 018 | 10/2021 |
| EP | 3 485 936 | 10/2021 |
| EP | 3 539 613 | 2/2022 |
| EP | 2 858 718 | 3/2022 |
| EP | 3 624 867 | 3/2022 |
| EP | 3 755 237 | 4/2022 |
| JP | 2013-013216 | 1/2013 |
| WO | WO 2008/106103 | 9/2008 |
| WO | WO 2009/023905 | 2/2009 |
| WO | WO 2009/029977 | 3/2009 |
| WO | WO 2010/042054 | 4/2010 |
| WO | WO 2011/007300 | 1/2011 |
| WO | WO 2012/147061 | 11/2012 |
| WO | WO 2015/152732 | 10/2015 |
| WO | WO 2017/021846 | 2/2017 |
| WO | WO 2017/066257 | 4/2017 |
| WO | WO 2017/089440 | 6/2017 |
| WO | WO 2017/118738 | 7/2017 |
| WO | WO 2017/165372 | 9/2017 |
| WO | WO 2017/218349 | 12/2017 |
| WO | WO 2018/033799 | 2/2018 |
| WO | WO 2018/100192 | 6/2018 |
| WO | WO 2019/025258 | 2/2019 |
| WO | WO 2019/025259 | 2/2019 |
| WO | WO 2019/025260 | 2/2019 |
| WO | WO 2019/101786 | 5/2019 |
| WO | WO 2019/145253 | 8/2019 |
| WO | WO 2019/158996 | 8/2019 |
| WO | WO 2019/183247 | 9/2019 |
| WO | WO 2019/185511 | 10/2019 |
| WO | WO 2019/185512 | 10/2019 |
| WO | WO 2019/211400 | 11/2019 |
| WO | WO 2019/211405 | 11/2019 |
| WO | WO 2019/211410 | 11/2019 |
| WO | WO 2019/211413 | 11/2019 |
| WO | WO 2019/211414 | 11/2019 |
| WO | WO 2019/211415 | 11/2019 |
| WO | WO 2019/211416 | 11/2019 |
| WO | WO 2019/229224 | 12/2019 |
| WO | WO 2019/234151 | 12/2019 |
| WO | WO 2019/241556 | 12/2019 |
| WO | WO 2019/244031 | 12/2019 |
| WO | WO 2020/089429 | 5/2020 |

* cited by examiner

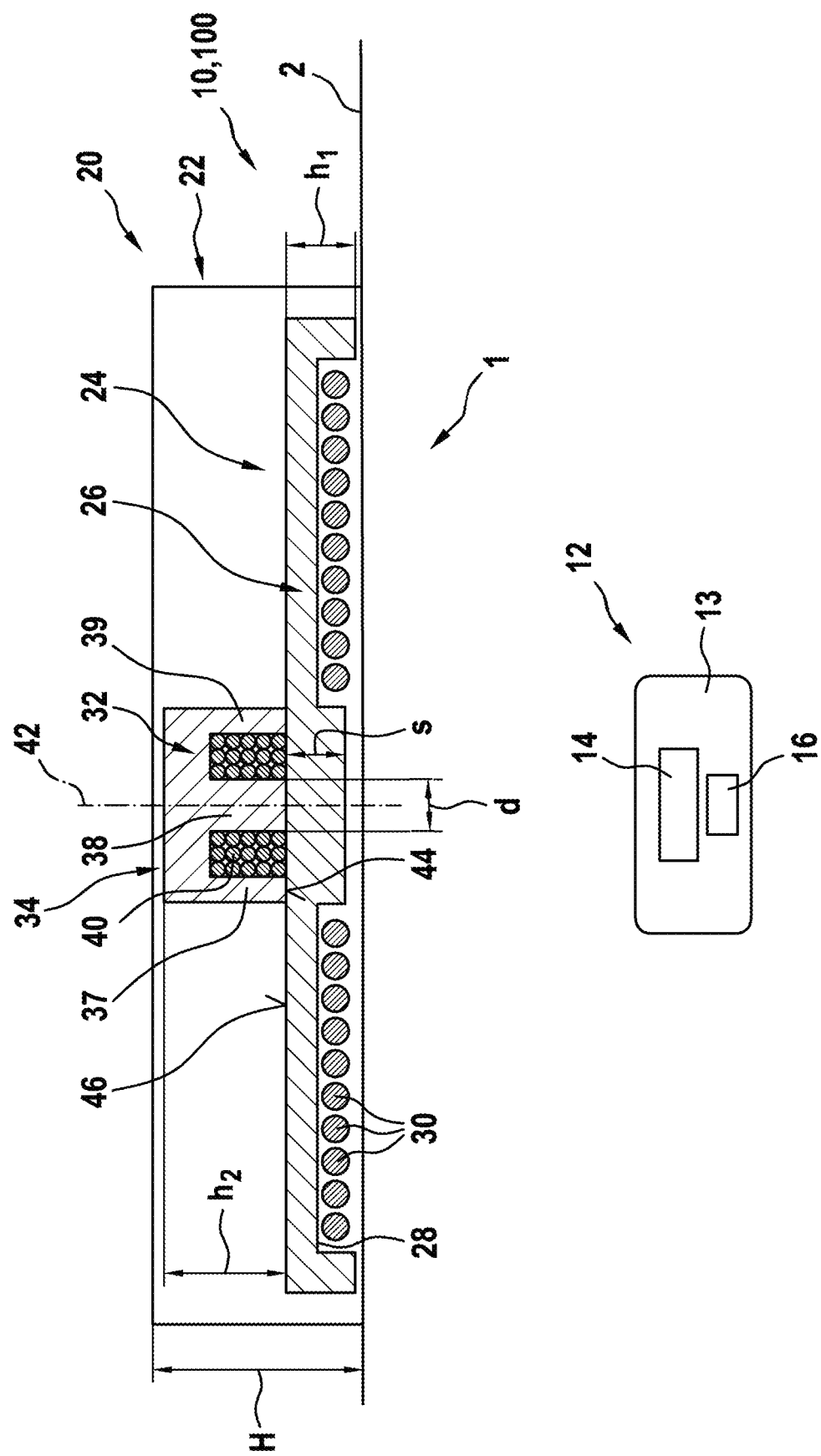

DEVICE FOR INDUCTIVE ENERGY TRANSMISSION IN A HUMAN BODY AND USE OF THE DEVICE

BACKGROUND

Field

The invention relates to a device for inductive energy transmission into a human body. The invention further relates to the use of a device according to the invention.

Description of the Related Art

Medical technology uses devices for inductive energy transmission, in which a transmitter unit disposed outside a human body comprises a transmitter coil, the magnetic field of which induces energy in the receiver coil of a receiver unit disposed [in] the human body, which at least indirectly serves to charge a battery disposed in the human body. Such a system is known as a so-called VAD (ventricular assist device) system used to operate a pump that supports the heart of a patient (DE 10 2016 106 683 A1).

For such a device, and this applies to both the receiver unit and the transmitter unit, it is essential that it is configured in as compact a manner as possible. On the one hand, in terms of the receiver unit, this minimizes the space required in the body for the receiver unit, while on the other hand, in terms of the transmitter unit, it increases the wearing comfort of such a transmitter unit under the patient's clothing. The transmitter unit or the receiver unit furthermore typically comprise a housing, in which the components of the respective unit are disposed. It is also known that, in addition to the transmitter coil or the receiver coil, an electronic circuit is required for the operation of said coils, which typically also comprises a so-called resonance or choke coil. Like the transmitter coil or the receiver coil, such a resonance or choke coil comprises a magnetic core and a wire winding that interacts with the magnetic core. In the case of the resonance or choke coil, this is typically a component of a resonance circuit and, in the state of the art, is always disposed discretely, i.e. separately from the transmitter coil or receiver coil, on a circuit carrier (circuit board) together with other electronic components. The separate arrangement and configuration of the magnetic cores for the transmitter coil or receiver coil and for the resonance or choke coil results in an increase of the overall height of the transmitter unit or receiver unit, in particular with regard to the respective magnetic cores, because the resonance or choke coil is disposed above or below the level of the transmitter coil or receiver coil and thus also affects the overall height of the housing of the transmitter unit or receiver unit.

SUMMARY

The device according to the invention for inductive energy transmission having the features of claim 1 has the advantage that it enables a particularly compact arrangement of the transmitter coil or receiver coil and the resonance or choke coil in the transmitter unit or the receiver unit.

The invention is based on the idea of using or configuring a part of the magnetic core of the transmitter coil or the receiver coil simultaneously as a part of the magnetic core of the resonance or choke coil or vice versa. This not only saves material for the magnetic cores, but also enables a particularly compact arrangement of the two magnetic cores relative to one another.

Advantageous further developments of the device for inductive energy transmission into a human body according to the invention are presented in the subclaims.

In a first structural configuration of the device, it is provided that the first magnetic core (of the transmitter or receiver coil) is disposed in direct contact with an end face of the second magnetic core (of the resonance or choke coil).

In order to fulfill the intended functionality, it is furthermore provided in a preferred structural configuration that the transmitter coil or the receiver coil comprises wire windings which are disposed concentrically to one another and the resonance or choke coil comprises second wire windings which are disposed concentrically to one another, and that the first wire windings are disposed radially outside the second wire windings.

The last-mentioned configuration in particular leads to a geometric arrangement, in which the resonance or choke coil is disposed concentrically to a longitudinal axis of the first magnetic core.

A structural arrangement or configuration of the two coils (transmitter coil and receiver coil or resonance or choke coil) as described thus far in particular enables a desired decoupling of the transmitter and the receiver coil with the resonance or choke coil due to both the selected topology and the design of the transmitter or receiver coil itself. The transmitter coil and the receiver coil in particular have a very low coupling factor to the resonance or choke coil, because the (magnetic) fields of the transmitter coil or receiver coil are enclosed on one side by the ferrite core. The return of the magnetic fields on the other side then takes place via the air over a longer distance and thus leads to the aforementioned low coupling. The structural arrangement of the coils as described thus far typically has a very low coupling factor of typically up to about 0.05.

Another preferred structural configuration provides that the first magnetic core is disc-shaped and has at least one groove-like recess which extends radially around the longitudinal axis for receiving first wire windings of the transmitter or receiver coil.

In particular in the last-mentioned design, it is further provided that the resonance or choke coil is disposed on the side of the at least one recess which faces away from the first wire windings.

To positively affect the saturation of the core material of the magnetic core of the resonance or choke coil and for the purpose of optimal guidance of the magnetic field lines, it is also advantageous if, in the region of contact with the second magnetic core, the first magnetic core has a wall thickness which corresponds to the wall thickness of a middle leg of the E-core of the second magnetic core.

The invention further also includes the use of a device for energy transmission into a human body according to the invention as described thus far, in particular as a component of a VAD system.

Further advantages, features and details of the invention emerge from the following description of preferred design examples and with reference to the drawing.

BRIEF DESCRIPTION OF THE DRAWING

The only FIGURE shows a schematic illustration of a device for inductive energy transmission into a human body.

DETAILED DESCRIPTION

The device 10 shown in the only FIGURE is in particular configured as a component of a so-called VAD system 100, wherein the VAD system 100 comprises a pump for supporting the heart function of a patient that is operated or supplied with energy via a not-depicted battery. This battery is charged by means of the device 10.

The device 10 comprises a receiver unit 12 that is disposed in a human body 1 and comprises a housing 13, in which a receiver coil 14, which is shown in the illustration of the FIGURE in a highly simplified manner, is disposed. The receiver coil 14 is used for at least indirect charging of said battery, for example via not-depicted wire connections to the battery and a not-depicted electronic circuit. In addition to the receiver coil 14, the receiver unit 12 further comprises a choke coil 16, which is likewise shown purely schematically and is not a component of a receiving oscillator circuit.

The receiver unit 12 interacts with a transmitter unit 20 disposed outside the body 1. As an example, the transmitter unit 20 comprises a housing 22 which, on the one hand, can be positioned in at least indirect contact with the skin 2 of the body 1 and in alignment with the receiver unit 12 and, on the other hand, comprises a transmitter coil 24 in its interior. The transmitter coil 24 consists of a disc-shaped first magnetic core 26, which comprises a radially circumferential, groove-like recess 28 on the side facing the receiver unit 12. First wire windings 30, which are disposed concentrically to one another around a longitudinal axis 42 of the first magnetic core 26, are disposed in the region of the recess 28 and serve to produce a not-depicted magnetic field in order to induce electrical energy in the receiver coil 12 which is used to charge said battery.

As an example, the transmitter coil 24 has a height h1. On the side of the first magnetic core 26 facing away from the receiver unit 12, a second magnetic core 32 is disposed as part of a resonance or choke coil 34. The second magnetic core 32 is configured in the form of an E-magnetic core 32. Second wire windings 40 of the resonance or choke coil 34 are concentrically wound around a (central) middle leg 38 of the second magnetic core 32.

As can be seen from the illustration of the FIGURE, the middle leg 38 is also disposed concentrically to the longitudinal axis 42 of the first magnetic core 26. The second wire windings 40 furthermore extend radially inside the first wire windings 30 of the transmitter coil 24.

With its three legs 37 to 39, the end face 44 of the second magnetic core 32 facing the first magnetic core 26 directly abuts the end face 46 of the first magnetic core 26. The illustration of the figure also shows that, in the region in which the second magnetic core 32 and the first magnetic core 26 overlap, the thickness d of the middle leg 38 of the second magnetic core 32 corresponds to the wall thickness s of the first magnetic core 26. The second magnetic core 32 has a height h2. The illustration of the figure further shows that the total height H of the housing 22 of the transmitter unit 20 substantially depends on or is determined by the sum of the two heights h1 and h2 of the two magnetic cores 26 and 32.

The device 10 as described thus far can be changed or modified in many ways without departing from the idea of the invention. It is in particular noted that the specific configuration of the transmitter coil 24 and the resonance or choke coil 34, or the magnetic cores 26, 32 thereof, has been described on the basis of the transmitter unit 20. It is just as possible for the described structure to be provided in the same way in the region of the receiver unit 12. This likewise results in a minimization of the overall height of the housing 13 of the receiver unit 12.

The invention claimed is:

1. A device for inductive energy transmission into a human body, the device comprising:
   a transmitter coil; and
   a receiver coil,
   wherein the transmitter coil and/or receiver coil includes a first magnetic core and a resonance or choke coil having a second magnetic core, the first and second magnetic cores configured to transmit or receive at least one magnetic field, wherein the first magnetic core is disc-shaped, comprises at least one recess extending radially around a longitudinal axis of the first magnetic core and configured to receive a plurality of wire windings, and forms a part of the second magnetic core, the second magnetic core comprising a middle leg along the longitudinal axis of the first magnetic core and at least one recess extending radially around the middle leg and configured to receive a plurality of wire windings.

2. The device according to claim 1, wherein the first magnetic core is disposed in direct contact with an end face of the second magnetic core.

3. The device according to claim 1, wherein the transmitter coil and/or the receiver coil comprises a plurality of first wire windings disposed concentrically relative to one another, wherein the resonance or choke coil comprises a plurality of second wire windings disposed concentrically relative to one another, and wherein the plurality of first wire windings are disposed radially outside the plurality of second wire windings.

4. The device according to claim 1, wherein the resonance or choke coil is disposed concentrically to the longitudinal axis of the first magnetic core.

5. The device according to claim 1, wherein the resonance or choke coil is disposed on a side of the recess, wherein the side of the recess faces away from the plurality of wire windings.

6. The device according to claim 1, wherein the second magnetic core comprises an E-magnetic core.

7. The device according to claim 2, wherein the first magnetic core comprises a region contacting the second magnetic core, wherein a wall thickness of the region of the first magnetic core corresponds to a thickness of the middle leg of the second magnetic core.

8. The device according to claim 1, wherein the resonance or choke coil is disposed on a side of the device facing away from a contact side of the transmitter coil and/or receiver coil.

9. A method for inductively transmitting energy into a human body, the method comprising:
   inductively transmitting energy into a human body using a device comprising:
   a transmitter coil; and
   a receiver coil,
   wherein the transmitter coil and/or receiver coil includes a first magnetic core and a resonance or choke coil having a second magnetic core, the first and second magnetic cores configured to transmit or receive at least one magnetic field, wherein the first magnetic core is disc-shaped, comprises at least one recess extending radially around a longitudinal axis of the first magnetic core and configured to receive a plurality of wire windings, and forms a part of the second magnetic core, the second magnetic core comprising a middle leg along the longitudinal axis of the first magnetic core and at least one recess extending radially around the middle leg and configured to receive a plurality of wire windings.

10. A device for inductive energy transmission into a human body, the device comprising:
- a transmitter coil; and
- a receiver coil,
- wherein the transmitter coil and/or receiver coil includes a first magnetic core and a resonance or choke coil having a second magnetic core, wherein the first magnetic core forms a part of the second magnetic core,
- wherein at least a region of the first magnetic core is disposed in direct contact with at least a region of an end face of the second magnetic core,
- wherein a thickness (s) of the region of the first magnetic core disposed in direct contact with at least a region of the end face of the second magnetic core corresponds to a thickness (d) of the middle leg of the second magnetic core,
- wherein the transmitter coil and/or receiver coil comprises a plurality of first wire windings disposed concentrically relative to one another in the at least one recess of the first magnetic core,
- wherein the resonance or choke coil comprises a plurality of second wire windings disposed concentrically relative to one another in the at least one recess of the second magnetic core, and
- wherein the plurality of first wire windings are disposed radially outside the plurality of second wire windings.

* * * * *